(12) United States Patent
McNamara et al.

(10) Patent No.: US 7,915,407 B2
(45) Date of Patent: Mar. 29, 2011

(54) PROCESS FOR {3-[2(R)-[(1R)-1-[3,5-BIS(TRIFLUORO METHYL)PHENYL]ETHOXY]-3(S)-(4-FLUOROPHENYL)MORPHOLIN-4-YL] METHYL]-5-OXO-4,5-DIHYDRO-[1,2,4]-TRIAZOL-1-YL}PHOSPHONIC ACID

(75) Inventors: James Michael McNamara, Fanwood, NJ (US); Louis Matty, Basking Ridge, NJ (US); Jonathan D. Rosen, Brooklyn, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/862,857

(22) Filed: Aug. 25, 2010

(65) Prior Publication Data

US 2010/0324287 A1 Dec. 23, 2010

Related U.S. Application Data

(62) Division of application No. 11/667,001, filed as application No. PCT/US2005/039946 on Nov. 3, 2005, now Pat. No. 7,807,829.

(60) Provisional application No. 60/625,209, filed on Nov. 5, 2004.

(51) Int. Cl.
*C07D 413/06* (2006.01)

(52) U.S. Cl. .................................................. 544/132
(58) Field of Classification Search ................... 544/132
See application file for complete search history.

(56) References Cited

U.S. PATENT DOCUMENTS 5,691,336 A * 11/1997 Dorn et al. ............... 514/236.2
5,780,467 A * 7/1998 Dorn et al. ............... 514/236.2

OTHER PUBLICATIONS

J.J. Hale et al., "Phosphorylated Morpholine Acetal Human Neurokinin-1- Receptor Antagonists as Water-Soluble Prodrugs", J. Med. Chem., 2000, vol. 43, pp. 1234-1241.*
T. D. Nelson et al., "Tetrabenzyl Pyrophosphate [{Diphosphoric Acid, Tetrakis (phenylmethyl) ester]}", Organic Syntheses, 2000, vol. 80, p. 219.*

* cited by examiner

*Primary Examiner* — Rebecca L Anderson
(74) *Attorney, Agent, or Firm* — Nicole M. Beeler; David A. Muthard

(57) ABSTRACT

The present invention is concerned with a process for the preparation of the compound {3-[2(R)-[(1R)-1-[3,5-bis(trifluoromethyl)phenyl]ethoxy]-3(S)-(4-fluorophenyl) -morpholin-4-yl]methyl]-5-oxo-4,5-dihydro-[1,2,4]-triazol-1-yl}phosphonic acid, and pharmaceutically acceptable salts thereof. This compound is useful as a substance P (neurokinin-1) receptor antagonist. In particular, the compound is useful e.g., in the treatment of emesis and inflammatory diseases.

19 Claims, No Drawings

PROCESS FOR {3-[2(R)-[(1R)-1-[3,5-BIS(TRIFLUOROMETHYL) PHENYL]ETHOXY]-3(S)-(4-FLUOROPHENYL) MORPHOLIN-4-YL]METHYL]-5-OXO-4,5-DIHYDRO-[1,2,4]-TRIAZOL-1-YL}PHOSPHONIC ACID

CROSS REFERENCE TO RELATED APPLICATIONS

This application is a divisional of U.S. Application No. 11/667,001, filed May 2 2007, now U.S. Pat. No. 7,807,829, which is a 371 of PCT/US2005/039946, filed Nov. 3, 2005, which claims benefit of U.S. Provisional Application No. 60/625,209, filed Nov. 5, 2004.

BACKGROUND OF THE INVENTION

The present invention relates to processes for the preparation of {3-[2(R)-[(1R)-1-[3,5-bis(trifluoromethyl)phenyl] ethoxy]-3(S)-(4-fluorophenyl)morpholin-4-yl]methyl]-5-oxo-4,5-dihydro-[1,2,4]-triazol-1-yl}phosphonic acid, a phosphoramidate derivative of aprepitant,

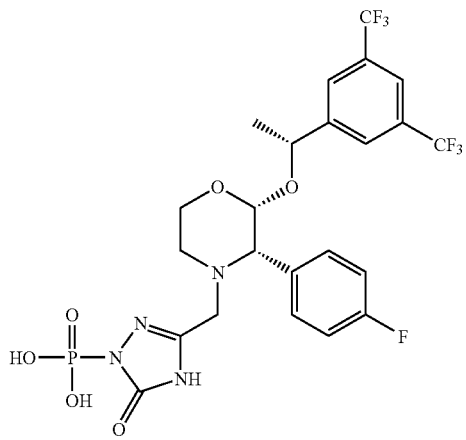

and pharmaceutically acceptable salts thereof, which is a useful therapeutic agent, specifically as a substance P (neurokinin-1) receptor antagonist.

This compound is disclosed as having therapeutic utility in U.S. Pat. Nos. 5,691,336 and 5,780,467 which also disclose processes of manufacture for this compound. In contrast to previously known processes, the present invention provides a more practical and economical method for preparing the compound in relatively high yield and purity. As such, there is a need for a process for the preparation of the compound that is cost-effective, amenable to large-scale production and utilizes readily available reagents.

SUMMARY OF THE INVENTION

The present invention relates to a process for preparing a compound of the formula I:

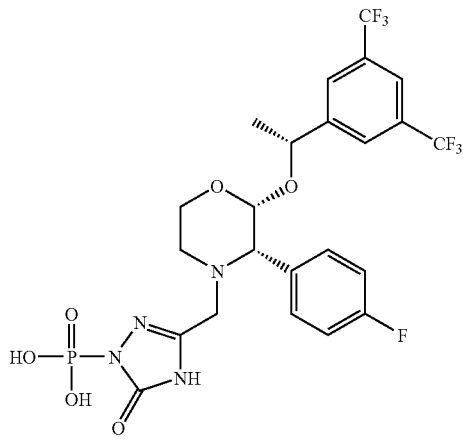

and pharmaceutically acceptable salts thereof,
by catalytic reduction of the corresponding mono-O-benzylphosphate compound.

The present invention further relates to a precipitation process for increasing the purity of a compound of the formula Ia:

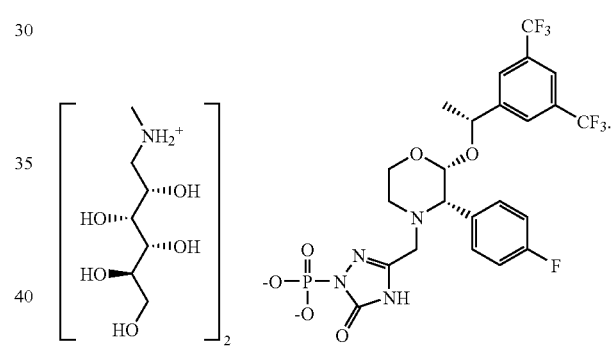

DETAILED DESCRIPTION OF THE INVENTION

The present invention is directed to a process for preparing a compound of the formula I:

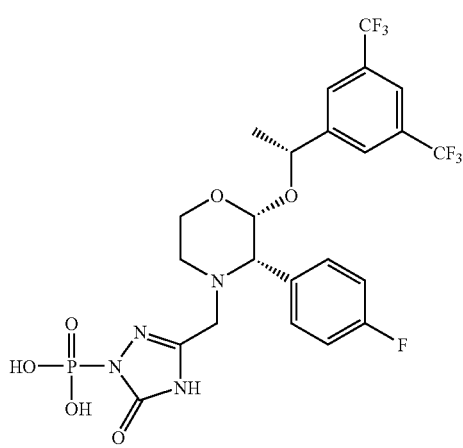

or a pharmaceutically acceptable salt thereof, comprising:

catalytic reduction of a compound of the formula II:

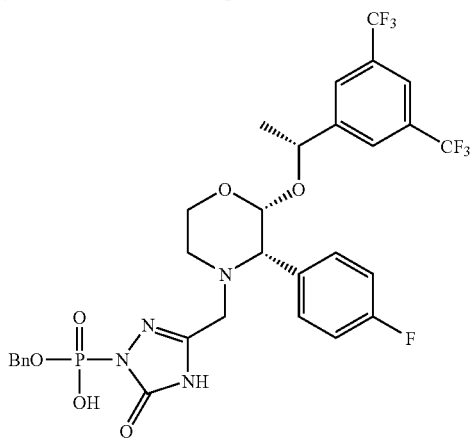

wherein Bn is benzyl,
optionally in the presence of the counterion of a pharmaceutically acceptable salt, to give the compound of formula Ia, or a pharmaceutically acceptable salt thereof.

The present invention is further directed to a process for preparing a compound of the formula I:

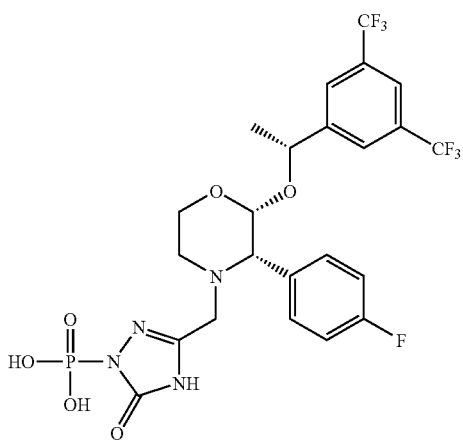

or a pharmaceutically acceptable salt thereof,
comprising:
(1) contacting the compound of the formula III:

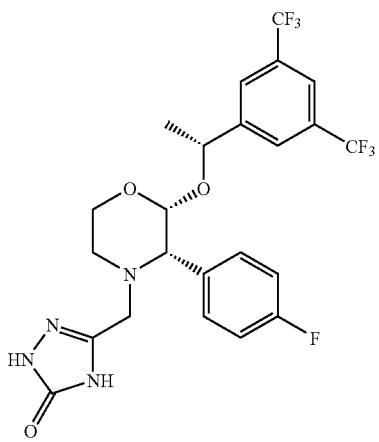

with tetrabenzyl pyrophosphate in the presence of a hindered base, and contacting the resultant product with methanol to give a compound of the formula II:

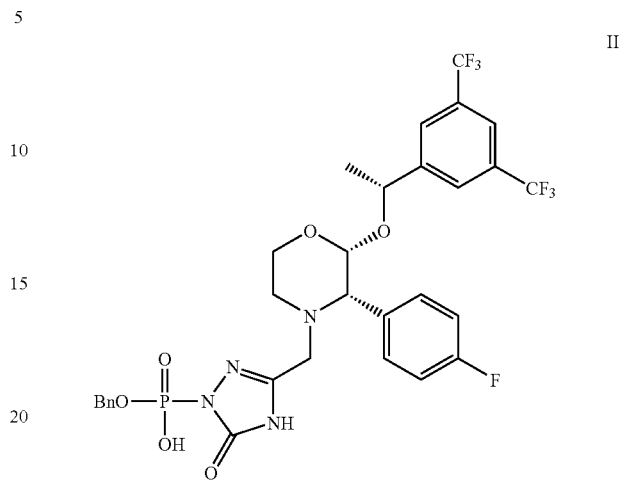

wherein Bn is benzyl; and
(2) catalytic reduction of the compound of the formula II in the presence of the counterion of a pharmaceutically acceptable salt, to give the compound of formula Ia.

In a further embodiment, the present invention is directed to a process for the preparation of {3-[2(R)-[(1R)-1-[3,5-bis(trifluoromethyl)phenyl]ethoxy]-3(S)-(4-fluoro-phenyl)morpholin-4-yl]methyl]-5-oxo-4,5-dihydro-[1,2,4]-triazol-1-yl}phosphonic acid N-methyl-D-glucamine of the formula Ia:

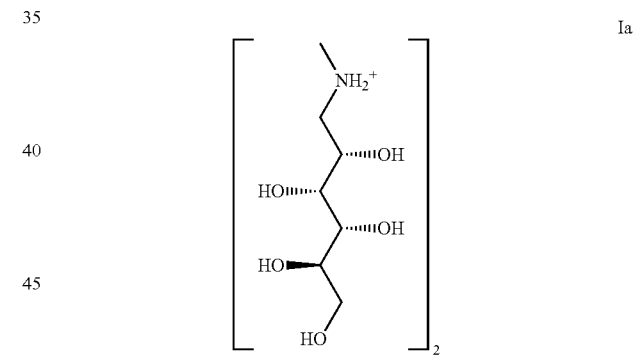

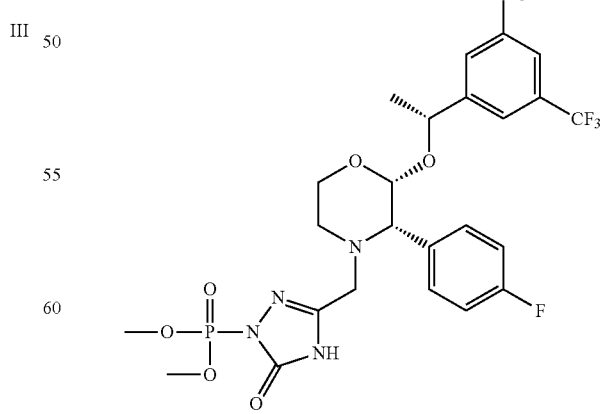

which comprises:
catalytic reduction of a compound of the formula II:

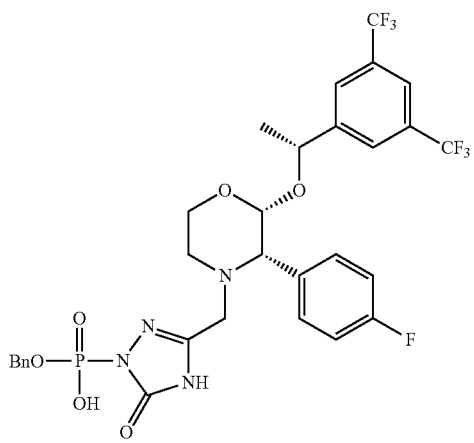

wherein Bn is benzyl, in the presence of N-methyl-D-glucamine, to give the compound of formula Ia.

In a further embodiment, the present invention is directed to a process for the preparation of {3-[2(R)-[(1R)-1-[3,5-bis(trifluoromethyl)phenyl]ethoxy]-3(S)-(4-fluoro-phenyl)morpholin-4-yl]methyl]-5-oxo-4,5-dihydro-[1,2,4]-triazol-1-yl}phosphonic acid N-methyl-D-glucamine of the formula Ia:

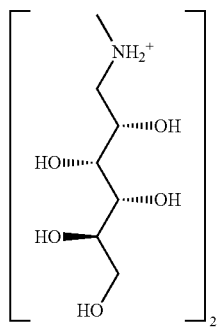

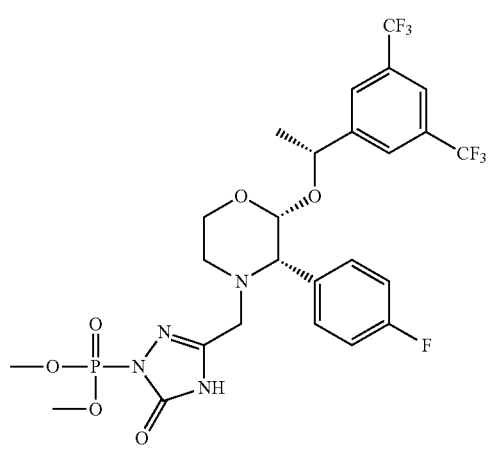

which comprises:

(1) contacting the compound of the formula III:

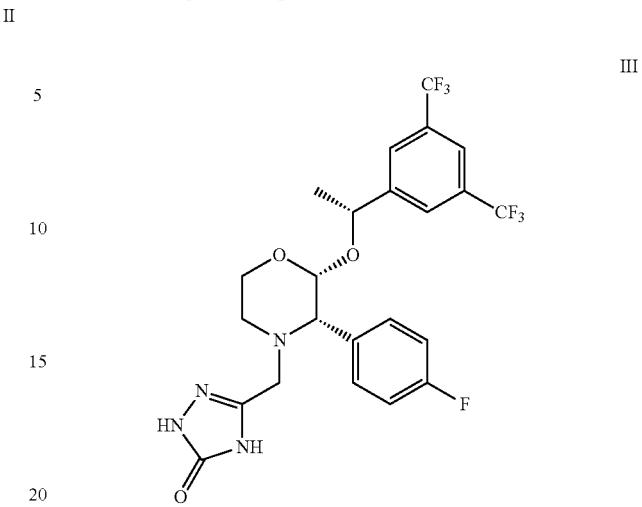

with tetrabenzyl pyrophosphate in the presence of a hindered base, and contacting the resultant product with methanol to give a compound of the formula II:

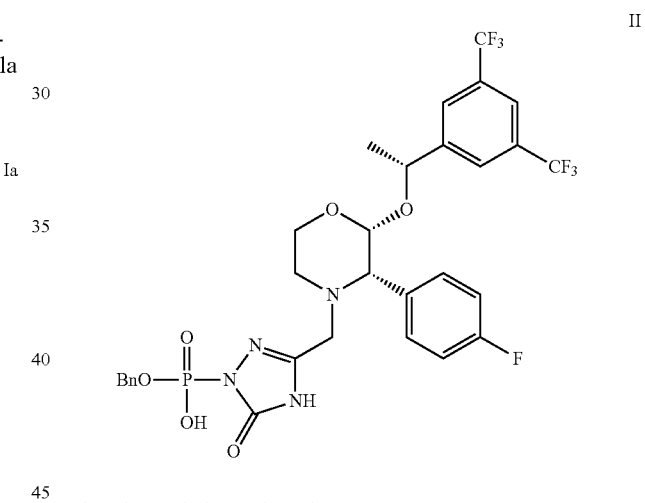

wherein Bn is benzyl; and (2) catalytic reduction of the compound of the formula II in the presence of N-methyl-D-glucamine, to give the compound of formula Ia.

In an embodiment of the present invention the step of contacting the compound of formula II with tetrabenzyl pyrophosphate in the presence of a hindered base, the hindered base is sodium hexamethyldisilazide (NaHMDS), potassium hexamethyldisilazide (KHMDS), lithium hexamethyldisilazide (LiHMDS), potassium t-butoxide, potassium t-pentoxide, potassium amylate, lithium diisopropylamide (LDA), lithium tetramethylpiperidide (LiTMP), sec-butyllithium, or tert-butyllithium. Within this embodiment, the hindered base is selected from sodium hexamethyldisilazide (NaHMDS), potassium hexamethyldisilazide (KHMDS) and lithium hexamethyldisilazide (LiHMDS). Further within this embodiment, the hindered base is sodium hexamethyldisilazide (NaHMDS).

Solvents for conducting the step of contacting the compound of formula II with tetrabenzyl pyrophosphate in the presence of a hindered base comprise an organic solvent. Within this embodiment, the organic solvent is selected from toluene, tetrahydrofuran (THF), diethyl ether, diglyme, dimethoxyethane (DME), and methyl t-butyl ether. Further within this embodiment, the organic solvent is tetrahydrofuran.

The step of contacting the compound of formula II with tetrabenzyl pyrophosphate in the presence of a hindered base is typically carried out at a temperature range of between about −20 and about 25° C. Within this embodiment, the temperature range is less than about 5° C. Further within this embodiment, the temperature range is between about −10 and about 5° C.

In an embodiment of the present invention the step of catalytic reduction of the compound of the formula II comprises catalytic hydrogenation. Within this embodiment, the step of catalytic reduction of the compound of the formula II comprises catalytic hydrogenation with a palladium catalyst, a platinum catalyst or a ruthenium catalyst. Within this embodiment, the step of catalytic reduction of the compound of the formula II comprises catalytic hydrogenation with a palladium catalyst. Within this embodiment, the step of catalytic reduction of the compound of the formula II comprises catalytic hydrogenation with a palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst). Within this embodiment, the step of catalytic reduction of the compound of the formula II comprises catalytic hydrogenation with a palladium on carbon catalyst. Further within this embodiment, the step of catalytic reduction of the compound of the formula II comprises catalytic hydrogenation with a 10% palladium on carbon catalyst or a 5% palladium on carbon catalyst. Further within this embodiment, the step of catalytic reduction of the compound of the formula II comprises catalytic hydrogenation with a 5% palladium on carbon catalyst.

Solvents for conducting the step of catalytic reduction of the compound of the formula II comprises a solvent which is selected from the group of $C_1$-$C_4$ primary, secondary and tertiary alcohols, and water. Within this embodiment, the solvent may comprise methanol, ethanol, isopropanol, n-propanol, n-butanol, water, and mixtures thereof. Further within this embodiment, the solvent comprises methanol, including mixtures of methanol and water.

In the present invention, it is preferred that the temperature of the reaction mixture for the catalytic reduction of the compound of the formula II is from about 10° C. to about 50° C., wherein the most preferred temperature is about 20-25° C.

In the present invention, it is preferred that the pressure of hydrogen during the catalytic reduction of the compound of the formula II is from about 1 to about 150 psi, wherein the most preferred pressure is about 5 to about 50 psi.

Optionally, following the catalytic reduction of the compound of the formula II to give the compound of formula I (or the compound of formula Ia), the solution of the compound of formula I (or the compound of formula Ia) is contacted with a tri-alkyl phosphine to remove the catalyst. Within this embodiment, the phosphine may be tri-n-butyl phosphine.

In another embodiment, the present invention is directed to a process for increasing the purity of a compound of the formula Ia:

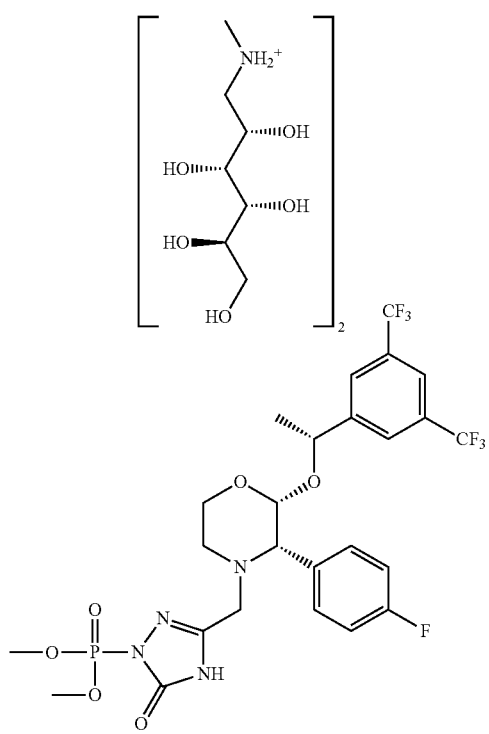

which comprises:
contacting a solution of the compound of formula Ia in methanol with an antisolvent which comprises acetonitrile to give the compound of formula Ia as a solid.

In a further aspect of this embodiment, the antisolvent which comprises acetonitrile further comprises an alcohol other than methanol. In a further aspect of this embodiment, the antisolvent which comprises acetonitrile further comprises an alcohol selected from ethanol, isopropanol, isobutanol and n-butanol. In a further aspect of this embodiment, the antisolvent which comprises acetonitrile further comprises an alcohol which is ethanol. In a further aspect of this embodiment, solution of the compound of formula Ia in methanol is added to a solution of acetonitrile:ethanol at approximately 50:50 (v/v), followed by addition of acetonitrile to increase the ratio of acetonitrile:ethanol to approximately 75:25 (v/v).

The present process for increasing the purity of a compound of the formula Ia by precipitation eliminates the need for lyophilization and/or spray drying, which would require the use of special equipment for large scale implementation.

In another embodiment, the present invention is directed to a compound of the formula:

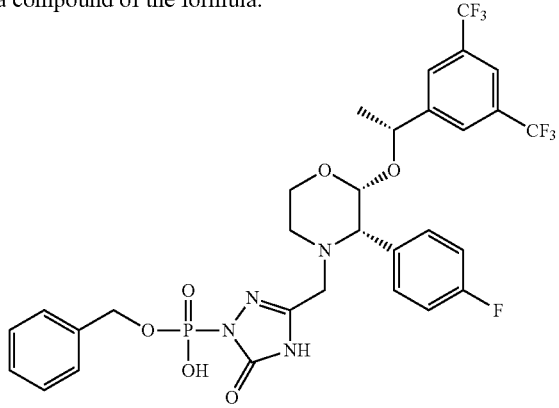

or a salt thereof.

Whereas the corresponding dibenzyl phosphoramidate compound is very unstable and is present as an amorphous material, this monobenzyl compound is a stable, crystalline solid. This crystalline penultimate intermediate is readily isolated by filtration, thereby eliminating the need for chromatographic purification, adsorption, nanofiltration, lyophilization, spray drying, or SCF precipitation of the final product. In addition, this crystalline penultimate intermediate allows a reduction in the catalyst loading for the step of catalytic hydrogenation. This crystalline penultimate intermediate also allows an increase in the amount of the counterion, such as N-methyl-D-glucamine, thereby increasing the purity of the compound of formula I prior to final isolation.

The term "pharmaceutically acceptable salts" refers to salts prepared from pharmaceutically acceptable non-toxic bases including inorganic or organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethyl-piperidine, glucamine, N-methyl-D-glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Particularly preferred is the N-methyl-D-glucamine salt. Salts in the solid form may exist in more than one crystal structure, and may also be in the form of hydrates.

The present process is surprisingly efficient, minimizing the production of side products, and increasing productivity and purity.

Aprepitant, 5-[[2(R)-[1(R)-[3,5-bis(trifluoromethyl)phenyl]ethoxy]-3(S)-(4-fluorophenyl)-4-morpholinyl]methyl]-1,2-dihydro-3H-1,2,4-triazol-3-one (i.e. [2R-[2α(R*),3α]]-5-[[2-[1-[3,5-bis(trifluoromethyl)phenyl]-ethoxy]-3-(4-fluorophenyl)-4-morpholinyl]methyl]-1,2-dihydro-3H-1,2,4-triazol-3-one), may be obtained in accordance with U.S. Pat. Nos. 5,637,699, 5,719,147, 6,096,742, 6,229,010, 6,255,545, 6,297,376, 6,350,915, 6,407,255, 6,469,164, 6,504,066, 6,538,134, 6,600,040, Hale, J. J.; et al. J. Med. Chem. 2000, 43, 1234-1241, or using modifications thereof. Tetrabenzyl pyrophosphate may be obtained in accordance with Nelson, T. D.; Rosen, J. D.; Bhupathy, M.; McNamara, J.; Sowa, M. J.; Rush, C.; Crocker, L. S. Org. Synth. 2003, 80, 219-226, or using modifications thereof. The starting material may be used directly or following purification. The following examples are provided for purposes of illustration and are not intended to limit the present invention.

EXAMPLE 1

Tetrabenzyl Pyrophosphate (TBPP)

A 12 L round-bottomed flask was equipped with an overhead stirrer, thermocouple, N2 inlet, and an addition funnel. The vessel was charged with dibenzyl phosphate (762 g) and isopropyl acetate (3 L). The slurry was cooled to 3±3° C. and then the 1.08 M dicyclohexylcarbodiimide (DCC) solution (1.30 L) was added via the addition funnel while maintaining the batch temperature at 3±3° C. Typical addition times were between 25-35 minutes and the reaction was typically complete within 30 minutes. The cold slurry was filtered and the dicyclohexylurea waste cake was rinsed (agitated) with isopropyl acetate (3×600 mL). The filtrate and rinses were combined and concentrated in vacuo to a final volume of 1.5 L. The batch was transferred to a 12 round-bottomed flask that was equipped with an overhead stirrer, thermocouple, N2 inlet, and an addition funnel. The batch was diluted with heptane (500 mL) and seeded with 1 mol % of tetrabenzyl pyrophosphate (8 g) to form a seed bed. Heptane (4.0 L) was then added to the stirred slurry at room temperature over 30 minutes. The batch was then cooled to 3±3° C. and aged for 1 hour. The slurry was filtered and the filter cake was washed with 20% isopropyl acetate/heptane (3×500 mL). The product cake was dried in vacuo and under a blanket of nitrogen overnight at room temperature. Tetrabenzylpyrophosphate was isolated (671 g, 1.25 mol, after correcting for seed) as a white crystalline solid (91% adjusted yield) which was stored in a freezer.

EXAMPLE 2

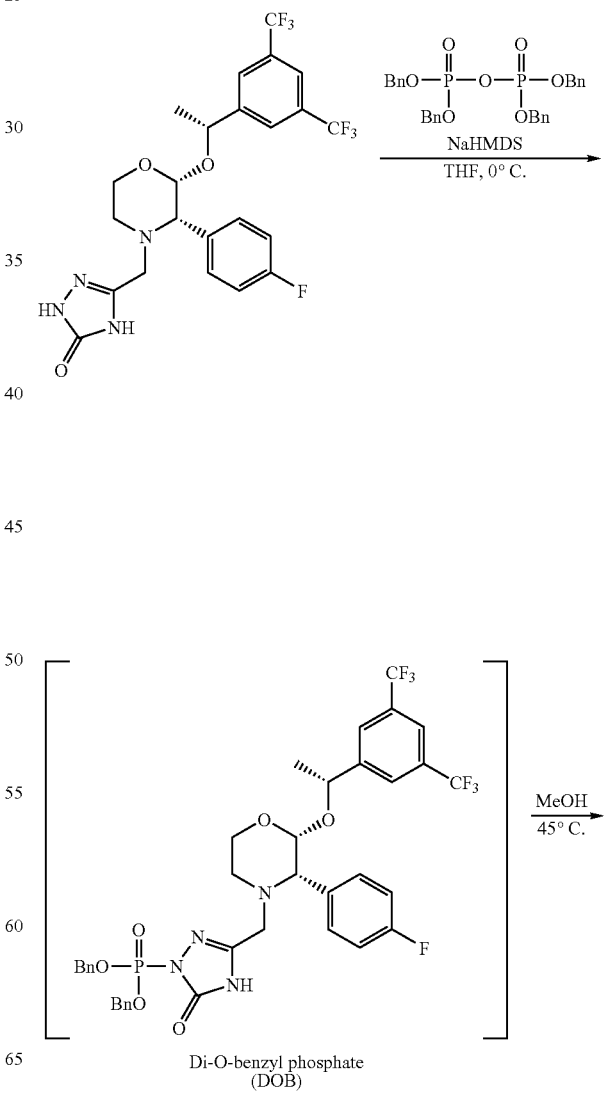

Di-O-benzyl phosphate (DOB)

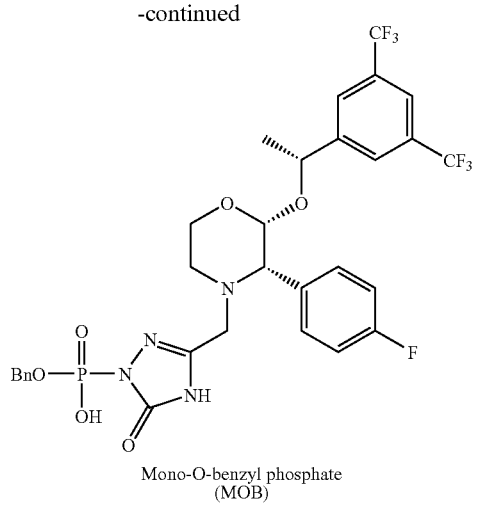

Mono-O-benzyl phosphate
(MOB)

Mono-O-benzylphosphate Intermediate (MOB)

A 12 L round-bottomed flask was equipped with an overhead stirrer, a thermocouple and a N2 inlet. The vessel was charged with aprepitant, 5-[[2(R)-[1(R)-[3,5-bis(trifluoromethyl)phenyl]ethoxy]-3(S)-(4-fluorophenyl)-4-morpholinyl]methyl]-1,2-dihydro-3H-1,2,4-triazol-3-one (300 g), tetrabenzyl pyrophosphate (393 g), and 3.85 L of dry THF. The batch was then cooled under N2 to an internal temperature of between −5 and 5° C. NaHMDS (1.37 L of a 1.0 M solution in THF) was added via an addition funnel at such a rate that the internal temperature remained <5° C. Typical addition times were 25-35 minutes and the reaction was typically complete in 60 minutes. Upon completion, the reaction was poured into a rapidly stirred mixture of t-butyl methyl ether (10.4 L) and saturated sodium bicarbonate (10.4 L). The two phase system was separated and the organic layer was washed with saturated sodium bicarbonate (1×10.4 L), 10% sodium bisulfate (1×5.2 L) and water (2×5.2 L). The batch was concentrated in vacuo (100 torr) to approximately half its original volume and then solvent switched to methanol (the final batch volume was 3.0 L). The internal batch temperature during the solvent switch was maintained at <25° C. This solution was transferred to a 5 L round-bottomed flask and heated to 45° C. while stirring under nitrogen. After 30 minutes, mono-O-benzylphosphate (3.0 g) was added and a seed bed should persist. The slurry was aged 18 hours at 45° C. The slurry was allowed to cool to room temperature and then aged one hour. The slurry was filtered through a sintered glass funnel and washed with methanol (2×1.2 L). The wet cake was dried in vacuo at room temperature, yielding 307 g (78%, adjusted for seed) mono-O-benzylphosphate intermediate as a white crystalline solid.

EXAMPLE 3

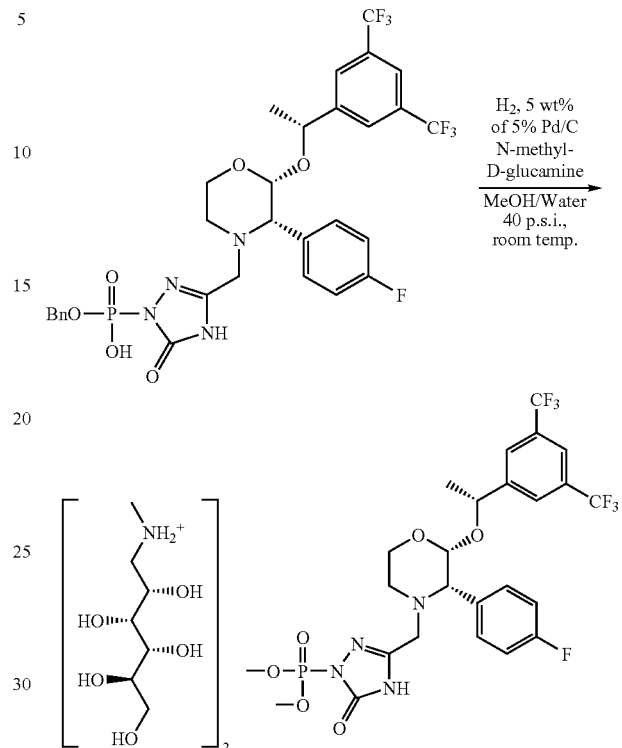

{3-[2(R)-[(1R)-1-[3,5-Bis(trifluoromethyl)phenyl]ethoxy]-3(S)-(4-fluorophenyl)morpholin-4-yl]methyl]-5-oxo-4,5-dihydro-[1,2,4]-triazol-1-yl}phosphonic acid N-Methyl-D-glucamine Salt The mono-O-benzylphosphate intermediate (300 g) and N-methyl-D-glucamine (166 g) were combined and dissolved in methanol (1.90 L) and water (110 mL). In a separate container, 5% Pd/C (15.0 g) was slurried in 350 mL methanol. This catalyst slurry was pre-reduced at room temperature and 40 p.s.i. after which the mono-O-benzylphosphate intermediate and glucamine slurry was added. The system was hydrogenated overnight. The crude hydrogenation slurry was filtered through a pad of solka floc and washed with MeOH (2×2 L). The filtrate was then concentrated in vacuo, maintaining the internal temperature at or below 18° C., to a final concentration of 200 g/L. This solution was carried forward into the precipitation.

EXAMPLE 4

Precipitation of {3-[2(R)-[(1R)-1-[3,5-Bis(trifluoromethyl)phenyl]ethoxy]-3(S)-(4-fluoro-phenyl)-morpholin-4-yl]methyl]-5-oxo-4,5-dihydro-[1,2,4]-triazol-1-yl}phosphonic acid N-Methyl-D-glucamine Salt A 2000 ml Pyrex bottle was setup with magnetic stirring and N2 blanket and capped. The batch post concentration was added to the bottle followed by tri-n-butylphosphine (300 μL). The batch was allowed to stir for about 12 hours at room temp. A 72 L RB flask was setup with overhead stirring, N₂ inlet, and temperature readout. Ethanol (21 L) and acetonitrile (21 L) were added to the flask and allowed to warm to RT. The solution of {3-[2(R)-[(1R)-1-[3,5-bis(trifluoromethyl)phenyl]ethoxy]-3(S)-(4-fluorophenyl)-morpholin-4-yl]methyl]-5-oxo-4,5-dihydro-[1,2,4]-triazol-1-yl}phosphonic acid N-methyl-D-glucamine salt in methanol was added to a 5000 ml dropping funnel via vacuum and 1 micron in-line filter. Then the batch was added to the antisolvent over 1 hour via dropping funnel. After the batch addition was complete, the slurry was aged for 15-30 minutes. The slurry was allowed to settle and as much supernatant as possible was decanted without removing solids. This volume (~30 L) was then replaced with an equal volume of 1:1 ethanol/acetonitrile and the slurry was agitated again for 30 minutes. A 3 L filter (medium frit, jacketed) was setup on a 50 L RB to collect the filtrate/wash. The solids were isolated on the filter and washed with ethanol/acetonitrile (1:1). The solids were dried on filter via nitrogen blow and transferred to a vacuum oven if needed. Yield was typically 340 g (79%).

EXAMPLE 5

Precipitation of {3-[2(R)-[(1R)-1-[3,5-Bis(trifluoromethyl)phenyl]ethoxy]-3 (S)-(4-fluoro-phenyl)-morpholin-4-yl]methyl]-5-oxo-4,5-dihydro-[1,2,4]-triazol-1-yl}phosphonic acid N-Methyl-D-glucamine Salt To a solution of {3-[2(R)-[(1R)-1-[3,5-bis(trifluoromethyl)phenyl]ethoxy]-3(S)-(4-fluorophenyl)-morpholin-4-yl]methyl]-5-oxo-4,5-dihydro-[1,2,4]-triazol-1-yl}phosphonic acid N-methyl-D-glucamine salt (356.4 g) in methanol was added tri-n-butyl phosphine (TBP) (1.7 ml) and aged over night under agitation at 20° C. (the TBP was added to remove excess dissolved Pd). The solution was then added to a mixture of 8.9 L acetonitrile and 8.9 L ethanol (KF<1000 ug/ml) at 20° C. over 1 hour. Acetonitrile (17.8 L) was then added to the batch over 120 minutes. The slurry was allowed to settle for 30 minutes before 70% of the supernatant was decanted and transferred to a filter. The remaining slurry was then re-suspended and pressure filtered. The wet cake was washed with neat acetonitrile (3.6 L) and the collected product was dried under vacuum at 20° C. Yield was typically 93%.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A process for preparing a compound of the formula I:

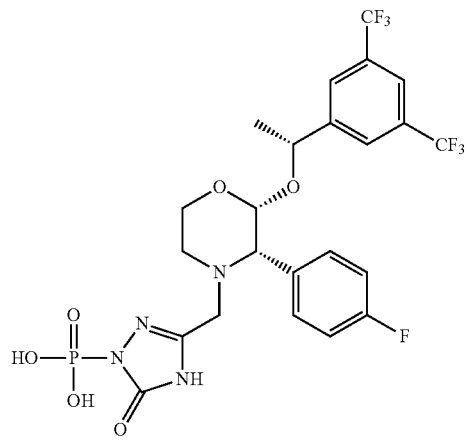

or a pharmaceutically acceptable salt thereof, which comprises:
catalytic reduction of a compound of the formula II:

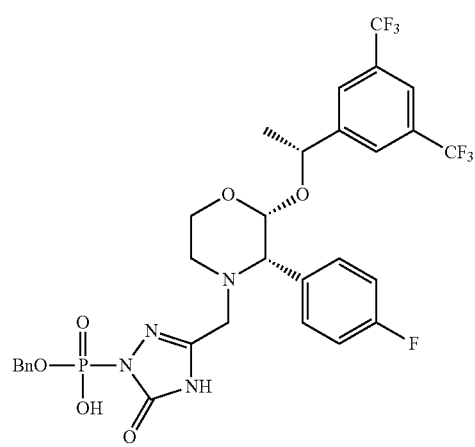

wherein Bn is benzyl,
optionally in the presence of the counterion of a pharmaceutically acceptable salt, to give the compound of formula I, or a pharmaceutically acceptable salt thereof.

2. The process of claim 1 for preparing a pharmaceutically acceptable salt of a compound of the formula I, wherein the pharmaceutically acceptable salt is of the formula Ia:

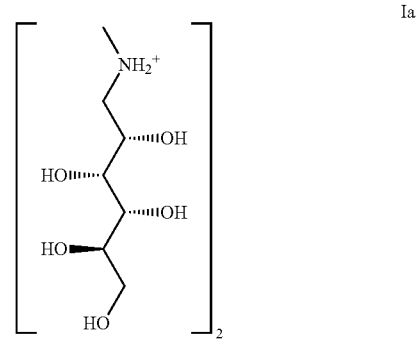

-continued

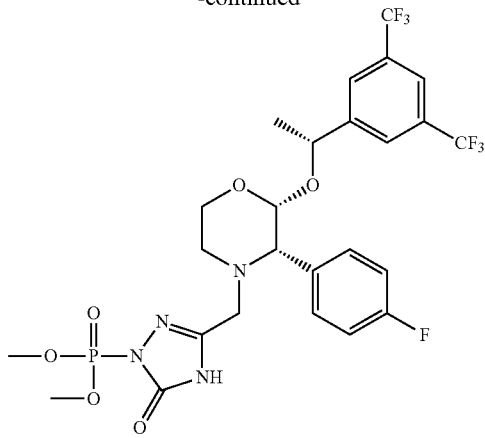

which comprises:
catalytic reduction of a compound of the formula II:

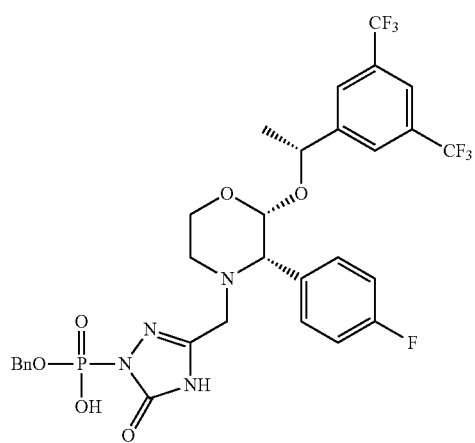

wherein Bn is benzyl,
in the presence of N-methyl-D-glucamine,
to give the compound of formula Ia.

3. The process of claim 1 which further comprises contacting the compound of the formula III:

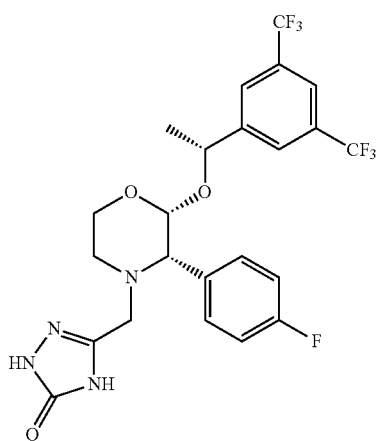

with tetrabenzyl pyrophosphate in the presence of a hindered base, and
contacting the resultant product with methanol to give the compound of the formula II:

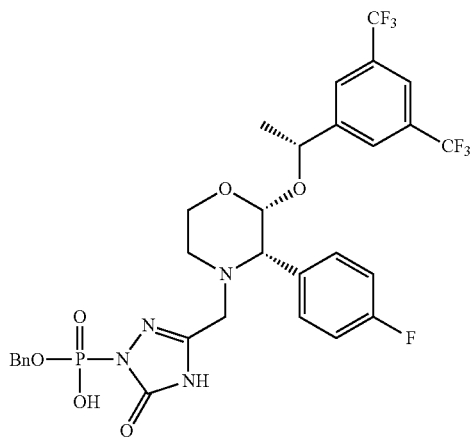

wherein Bn is benzyl.

4. The process of claim 2 which further comprises contacting the compound of the formula III:

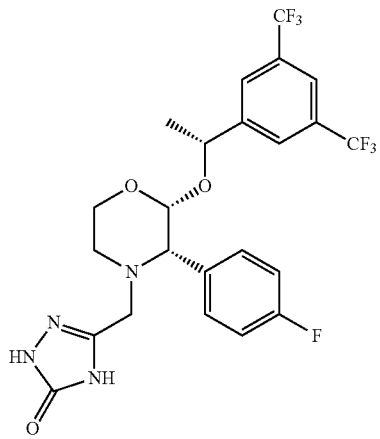

with tetrabenzyl pyrophosphate in the presence of a hindered base, and contacting the resultant product with methanol to give the compound of the formula II:

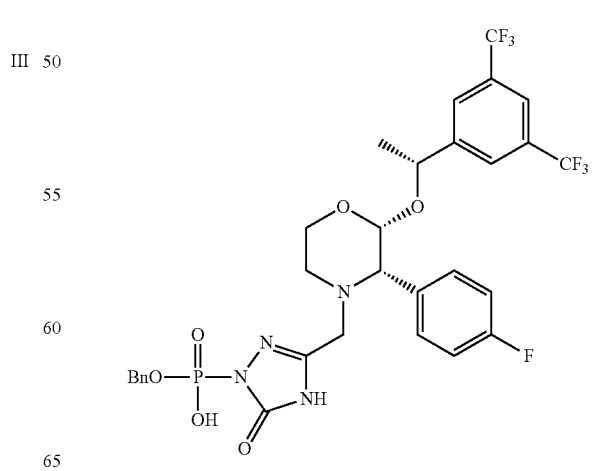

wherein Bn is benzyl.

5. The process of claim 3 wherein the hindered base is selected from: sodium hexamethyldisilazide, potassium hexamethyldisilazide, lithium hexamethyldisilazide, potassium t-butoxide, potassium t-pentoxide, potassium amylate, lithium diisopropylamide, lithium tetramethylpiperidide, sec-butyllithium, and tert-butyllithium.

6. The process of claim 5 wherein the hindered base is selected from: sodium hexamethyldisilazide, potassium hexamethyldisilazide, lithium hexamethyldisilazide, lithium diisopropylamide and lithium tetramethylpiperidide.

7. The process of claim 6 wherein the hindered base is selected from sodium hexamethyldisilazide, potassium hexamethyldisilazide and lithium hexamethyldisilazide.

8. The process of claim 7 wherein the hindered base is sodium hexamethyldisilazide.

9. The process of claim 4 wherein the hindered base is selected from sodium hexamethyldisilazide, potassium hexamethyldisilazide and lithium hexamethyldisilazide.

10. The process of claim 9 wherein the hindered base is sodium hexamethyldisilazide.

11. The process of claim 1 wherein the catalytic reduction of the compound of the formula II comprises catalytic hydrogenation with a palladium catalyst, a platinum catalyst or a ruthenium catalyst.

12. The process of claim 11 wherein the catalytic reduction of the compound of the formula II comprises catalytic hydrogenation with a palladium catalyst which is selected from: palladium on carbon, palladium on alumina, palladium on barium sulfate, palladium on calcium carbonate, palladium on barium carbonate, palladium on strontium carbonate, palladium on silica, and palladium hydroxide on carbon.

13. The process of claim 12 wherein the catalytic reduction of the compound of the formula II comprises catalytic hydrogenation with a palladium catalyst which is a palladium on carbon catalyst.

14. The process of claim 2 wherein the catalytic reduction of the compound of the formula II comprises catalytic hydrogenation with a palladium catalyst which is a palladium on carbon catalyst.

15. The process of claim 1 which further comprises contacting the compound of formula I with a tri-alkyl phosphine.

16. The process of claim 2 which further comprises contacting the compound of formula Ia with a tri-alkyl phosphine.

17. The process of claim 2 which further comprises contacting a solution of the compound of formula Ia in methanol with an antisolvent which comprises acetonitrile to give the compound of formula Ia as a solid.

18. The process of claim 17 wherein the antisolvent comprises acetonitrile and an alcohol selected from ethanol, isopropanol, isobutanol and n-butanol.

19. The process of claim 18 wherein the antisolvent comprises acetonitrile and ethanol.

* * * * *